United States Patent
Pfister et al.

[11] Patent Number: 5,874,434
[45] Date of Patent: Feb. 23, 1999

[54] 10,11-METHANODIBENZOSUBERANE DERIVATIVES

[75] Inventors: Jurg R. Pfister, Los Altos; Doris L. Slate, Mountain View, both of Calif.

[73] Assignee: Syntex (U.S.A.) Inc., Palo Alto, Calif.

[21] Appl. No.: 792,746

[22] Filed: Feb. 3, 1997

Related U.S. Application Data

[63] Continuation of Ser. No. 49,065, Apr. 19, 1993, Pat. No. 5,643,909.

[51] Int. Cl.$^6$ .................................... A61K 31/50
[52] U.S. Cl. ............................................. 514/253
[58] Field of Search ............................... 514/253

[56] References Cited

U.S. PATENT DOCUMENTS 5,643,909  7/1997  Pfister et al. .

*Primary Examiner*—Alan Siegel
*Attorney, Agent, or Firm*—Heller Ehrman White & McAuliffe

[57] ABSTRACT

10,11-Methanodibenzosuberane derivatives, i.e., the compounds of Formula I:

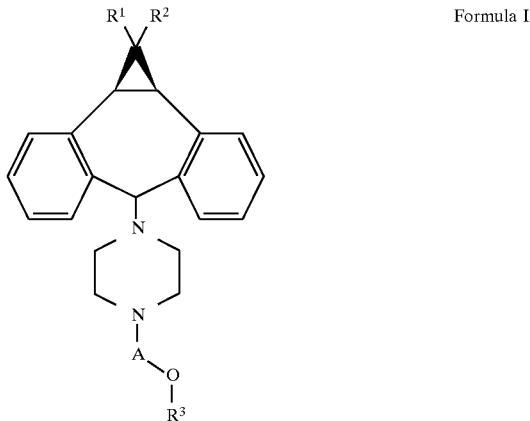

Formula I wherein:

A is —$CH_2$—$CH_2$—, —$CH_2$—$CHR^a$—$CH_2$—, or —$CH_2$—$CHR^a$—$CHR^b$—$CH_2$—, where one of $R^a$ or $R^b$ is H, OH, or lower acyloxy, and the other is H;

$R^1$ is H, F, Cl or Br;

$R^2$ is H, F, Cl or Br; and $R^3$ is heteroaryl or phenyl optionally substuted with F, Cl, Br, $CF_3$, CN, $NO_2$ or $OCHF_2$;

and the pharmaceutically acceptable salts thereof, are useful chemosensitizing agents, e.g., for cancer chemotherapy, particularly for treating multidrug resistance.

8 Claims, No Drawings

10,11-METHANODIBENZOSUBERANE DERIVATIVES

This is a continuation of application Ser. No. 08/049,065 Apr. 19, 1993 now U.S. Pat. No. 5,643,909.

FIELD OF THE INVENTION

The present invention relates to pharmaceutically active agents (e.g., for the treatment of cancer), particularly to drugs enhancing the efficacy of existing cancer chemotherapeutics and for treating multidrug resistance, and specifically to a series of 10,11-methanodibenzosuberane derivatives. The invention is also directed to pharmaceutical formulations and chemosensitizing methods, e.g., for treating cancer including the reversal of multidrug resistance.

BACKGROUND INFORMATION

Among the problems faced in cancer chemotherapy is the development of resistance to treatment regimens. Tumors that respond well to a particular drug or drugs initially, often develop a tolerance to the drug(s). This disease state, called multi-drug resistance, is discussed in greater detail in Kuzmich and Tew, "Detoxification Mechanisms and Tumor Cell Resistance to Anticancer Drugs," particularly section VII "The Multidrug-Resistant Phenotype (MDR)," *Medical Research Reviews*, Vol. 11, No. 2, 185–217, particularly 208–213 (1991); and in Georges, Sharom and Ling, "Multidrug Resistance and Chemosensitization: Therapeutic Implications for Cancer Chemotherapy," *Advances in Pharmacology*, Vol. 21, 185–220 (1990).

Certain active agents, called chemosensitizing agents or potentiating agents, have been suggested as resistance modifying agents for treating multidrug resistance, but have suffered from various disadvantageous properties. These have included, e.g., verapamil (a calcium entry blocker that lowers blood pressure and has also been found effective in vitro for treating drug-resistant malaria), steroids, trifluoperazine (a CNS agent), vindoline, and reserpine (an α-2 blocker with CNS properties). Thus, there has remained a need for active agents to treat, i.e., reverse, inhibit and/or prevent multidrug resistance, preferably with minimal or no adverse side effects.

Chemosensitizing agents interact with P-glycoprotein, a drug efflux pump found in cell membranes, particularly those of multidrug resistant tumor cells, gastrointestinal tract cells, and the endothelial cells that form the blood brain barrier. By blocking this pump, chemosensitizing agents inhibit the efflux of cancer chemotherapeutic drugs from tumor cells, and can enhance permeation of nutrients or active agents through the gastrointestinal tract, and the permeation of active agents through the blood brain barrier.

U.S. Pat. No. 5,112,817 to Fukazawa et al. discloses certain quinoline derivatives useful as anticancer drug potentiators for the treatment of multidrug resistance. One of the initially promising active agents there-disclosed is MS-073, which has the following structure:

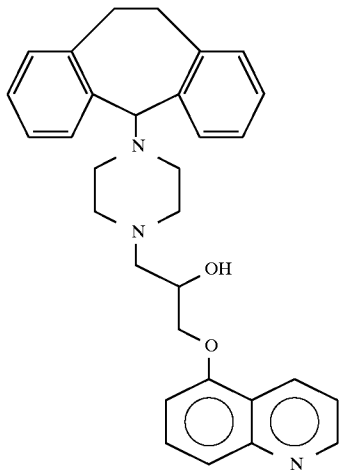

MS-073

While highly active in in vitro testing, MS-073 was, however, found to have poor oral bioavailability and to suffer from instability problems in solution. Other compounds of the series, such as the biphenylmethylcarbonyl derivative MS-209, have been found to have better stability and oral bioavailability, but, at the cost of having to administer higher effective doses. Thus, it has remained desired to provide an anticancer drug potentiator having the activity of MS-073, together with good oral bioavailability and stability.

SUMMARY OF THE INVENTION

One aspect of the present invention concerns 10,11-methanodibenzosuberane derivatives, i.e., the compounds of Formula I:

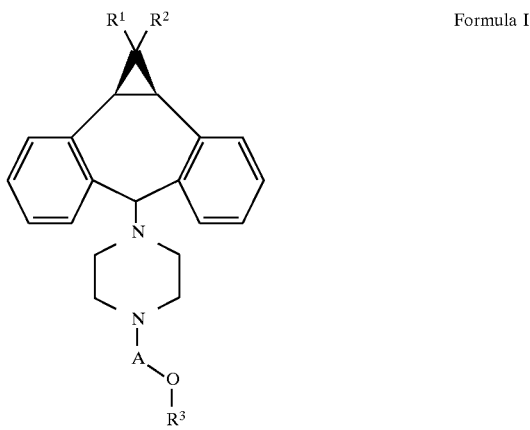

Formula I wherein:

A is $-CH_2-CH_2-$, $-CH_2-CHR^a-CH_2-$ where $R^a$ is H, OH or lower acyloxy, or $-CH_2-CHR^a-CHR^b-CH_2-$, where one of $R^a$ or $R^b$ is H, OH, or lower acyloxy, and the other is H;

$R^1$ is H, F, Cl or Br;

$R^2$ is H, F, Cl or Br; and $R^3$ is heteroaryl or phenyl optionally substituted with F, Cl, Br, $CF_3$, CN, $NO_2$ or $OCHF_2$;

and the pharmaceutically acceptable salts thereof.

In a preferred aspect, the invention relates to certain compounds of Formula I, and in particular to the single isomers thereof, particularly including the compound where A is $-CH_2-CHR^a-CH_2-$ where $R^1$ is OH, $R^1$ is F, $R^2$ is F, and $R^3$ is quinoline. Most preferred is the (2R)-anti isomer.

In another aspect, the invention relates to a pharmaceutical composition containing a therapeutically effective amount of a compound of Formula I or a pharmaceutically acceptable salt thereof and a pharmaceutically acceptable excipient.

In still another aspect, the invention relates to a method of treament by administering to a mammal in need of such treatment a compound of Formula I or a pharmaceutically acceptable salt thereof in an amount therapeutically effective to potentiate the efficacy of a co-administered cancer chemotherapeutic agent.

In yet another aspect, the invention relates to a method of treating drug resistance in a mammal, by administering to a mammal in need thereof a therapeutically effective amount of a compound of Formula I or a pharmaceutically acceptable salt thereof. One embodiment of this aspect entails a method of treating drug-resistant malaria. In a preferred embodiment, a method of treating multidrug resistant cancer in a mammal evidencing clinical resistance to a cancer chemotherapeutic agent, a resistance modifying amount of a compound or salt of Formula I is co-administered with a therapeutically effective amount of the cancer chemotherapeutic agent to which resistance has been evidenced.

In still another aspect the invention relates to a chemosensitizing method for enhancing bioavailability of a pharamceutically active agent comprising administering to a mammal in need thereof an amount of a compound or salt of Formula I sufficient to increase permeation of an active agent through the blood-brain barrier or the gastrointestinal tract.

DETAILED DESCRIPTION OF THE INVENTION

Definitions and General Parameters

The following definitions are set forth to illustrate and define the meaning and scope of the various terms used to describe the invention herein.

The term "alkyl" refers to a fully saturated monovalent radical containing only carbon and hydrogen, and which may be a cyclic, branched or straight chain radical. This term is further exemplified by radicals such as methyl, ethyl, t-butyl, pentyl, pivalyl, heptyl and adamantyl.

The term "lower alkyl" refers to a cyclic, branched or straight chain monovalent alkyl radical of one to six carbon atoms. This term is further exemplified by such radicals as methyl, ethyl, n-propyl, isopropyl, n-butyl, t-butyl, i-butyl (or 2-methylpropyl), cyclopropylmethyl, i-amyl, n-amyl, and hexyl.

The term "alkylene" refers to a fully saturated divalent radical containing only carbon and hydrogen, and which may be a branched or straight chain radical. This term is further exemplified by radicals such as methylene, ethylene, n-propylene, t-butylene, i-pentylene, and n-heptylene.

The term "lower alkylene" refers to a divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "lower acyloxy" refers to the group —O—C (O)—$R^1$ where $R^1$ is lower alkyl.

The term "aryl" refers to a monovalent unsaturated aromatic carbocyclic radical having a single ring (e.g., phenyl) or two condensed rings (e.g., naphthyl), which can optionally be mono- , di- or tri-substituted, independently, with fluoro, chloro, bromo, trifluoromethyl, cyano, nitro and/or difluoromethoxy.

The term "heteroaryl" refers to a monovalent unsaturated aromatic carbocyclic radical having at least one hetero atom, such as N, O or S, within the ring, such as quinolyl, benzofuranyl and pyridyl.

The term "halo" refers to fluoro, bromo, chloro and iodo.

"Optional" or "optionally" means that the subsequently described event or circumstance may or may not occur, and that the description includes instances where said event or circumstance occurs and instances in which it does not.

A "pharmaceutically acceptable salt" may be any salt derived from an inorganic or organic acid. The term "pharmaceutically acceptable anion" refers to the anion of such acid addition salts. The salt and/or the anion are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount" means a dosage sufficient to provide treatment for the disease state being treated. This will vary depending on the patient, the disease and the treatment being effected.

The term "co-administer" means the administration of more than one active agent as part of the same treatment regimen, whether they are administered simultaneously or at different times.

"Structure of Formula I" refers to the generic structure of the compounds of the invention. The chemical bonds indicated as with a wavy line, e.g., in Formula II indicate nonspecific stereochemistry, e.g. at position 5 of the dibenzosuberane, i.e., the carbon to which is attached the piperazine group.

"Isomerism" refers to compounds having the same atomic mass and atomic number but differing in one or more physical or chemical properties.

"Stereoisomer" refers to one of two chemical compounds having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation.

"Optical isomerism" describes one type of stereoisomerism which manifests itself by the rotation that the isomer, either pure or in solution, imparts to the plane of polarized light. It is caused in many instances by the attachment of four different chemical atoms or groups to at least one of the carbon atoms in a molecule. These isomers may be described as d- , 1- , or a d, 1-pair or D-, L- or a D,L-pair; or (R)-, (S)-, or an (R,S)-pair, depending upon the nomenclature system employed.

The compounds of Formula I exist in two isomeric configurations defined by the relationship of the 10,11-methano and the 5-piperazinyl substituents on the dibenzosuberane (see, is for example, the structure represented in Formula II, in the Nomenclature description which follows). When the 10,11-methano and the 5-piperazinyl substituents are both oriented in the same direction vis-a-vis the dibenzosuberane (e.g., both up or both down) the isomeric form is called "syn." When the 10,11-methano and the 5-piperazinyl substituents are oriented in opposite directions vis-a-vis the dibenzosuberane (e.g., one up and the other down) the isomeric form is called "anti."

Certain compounds of Formula I will have an asymmetric center within the group identified as "A" where $R^a$ or $R^b$ is not hydrogen. These compounds can exist in two stereochemical forms, called (+) and (−) or called (R)- and (S)-, or as mixtures of the two stereoisomers. The (R)- and (S)- designation will be used in this application.

While specific stereoisomers are disclosed and named, the present invention is to be interpreted to include the individual stereoisomers as well as mixtures, racemic and otherwise, thereof.

Nomenclature

The compounds of Formula I are named and numbered as described below with reference to Formula II.

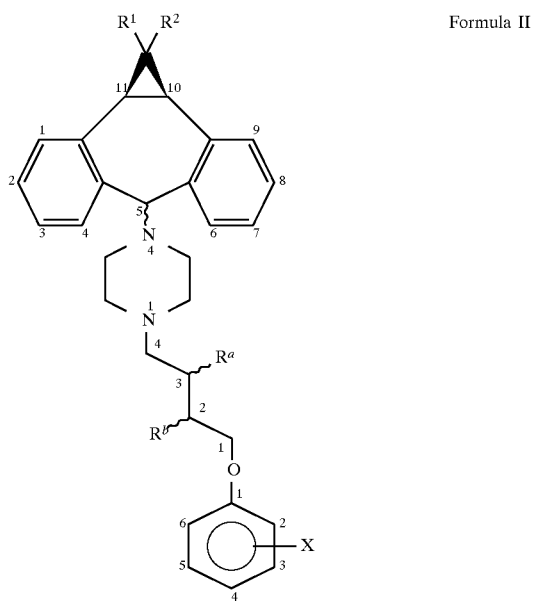

Formula II

For example, the compound where $R^1$ and $R^2$ are chloro, $R^1$ is hydroxy, and the phenyl group (of $R^3$ in Formula 1) is substituted at the 3-position with $NO_2$ is named (3R,S)-anti, syn-1-{4-[4-(10,11-dichloromethanodibenzosuber-5-yl)piperazin-1-yl]-3-hydroxybutoxy}-3-nitrobenzene.

The compound where $R^1$ and $R^2$ are hydrogen, $R^6$ is acetoxy (in the isomeric form going down into the page), the phenyl group (of $R^3$ in Formula 1) is substituted at the 5-position with trifluoromethyl, and the bond connecting the 4-position of the piperazine to the 5-position of the benzosuberane is in the isomeric form going up from the page, is named (2S)-syn-1-{4-[4-(10,11-methanodibenzosuber-5-yl)piperazin-1-yl]-2-acetoxybutoxy}-5-trifluoromethylbenzene.

A preferred compound of the invention, illustrated below as Formula III:

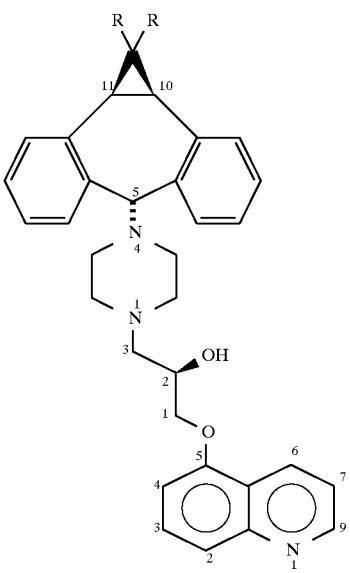

Formula III which is the compound of Formula I wherein $R^1$ and $R^2$ are F, A is (2R)-hydroxypropyl, and $R^3$ is quinolyl attached at the 5-position to the oxygen, is named (2R)-anti-5-{3-[4-(10,11-difluoromethano-dibenzosuber-5-yl)piperazin-1-yl]-2-hydroxypropoxy}quinoline. Alternatively, the Chemical Abstracts nomenclature for the compound of Formula III is 1-(4-anti(1,1-difluoro-1a,10b-dihydrodibenzo[a,e]cyclopropa[c]cyclohepten-6-yl)piperazin-1-yl)-(2R)-3-(5-quinolyloxy)-2-propanol (the numbering represented in Formula III does not apply for the Chemical Abstracts nomenclature system). While either nomenclature system adequately describes the compounds of the present invention, the former system will be employed for purposes of the present specification.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 5° C. to 100° C. (preferably from 10° C. to 50° C.; most preferably at "room" or "ambient" temperature, e.g., 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures.

Specific illustrations of suitable separation and isolation procedures can be had by reference to the examples hereinbelow. However, other equivalent separation or isolation procedures can, of course, also be used.

Synthesis of the Compounds of Formula I

The compounds of Formula I can be prepared by following the procedures described in U.S. Pat. No. 5,112,817, incorporated herein by reference, by substituting the dibenzosuberone with an optionally substituted 10,11-methanodibenzosuberone, prepared, for example, as described in Ciganek, et al., "Imine Analogues of Tricyclic Antidepressants," *J.Med.Chem.*, 1981, 24, 336–41; or in Coyne and Cusic, "Aminoalkyldibenzo[a,e]cyclopropa[c] cycloheptene Derivatives. A Series of Potent Antidepressants," *J.Med.Chem.*, 1974, Vol. 17, No. 1, 72–75, both incorporated herein by reference. Alternative syntheses of the compounds of Formula I are described below with reference to Reaction Schemes 1, 2 and 3.

BRIEF DESCRIPTION OF REACTION SCHEMES

Reaction Scheme 1 illustrates synthesis of the compounds of Formula I where $R^a$ is H or OH.

Reaction Scheme 2 illustrates synthesis of the compounds of Formulae 8 and 9; these are employed as reactants in Step 5 of Reaction Scheme 1 as precursors in the synthesis of the compounds of Formula I.

Reaction Scheme 3 illustrates synthesis of the compounds of Formula I where $R^b$ is OH.

As used in the Reaction Schemes, the substituents A, $R^1$, $R^2$, $R^3$, $R^a$ and $R^b$ have the same meaning as described in the Summary of the Invention. The substituent "X" indicates a halo group; n is 1 or 2; and m is 1, 2, 3 or 4.

Starting Materials

The compound 5H-dibenzo[a,d]cyclohepten-5-one [also named dibenzo[a,d]-5H-cyclohepten-5-one or dibenzosuberenone) is commercially available, e.g., from Aldrich Chemical Company, Milwaukee, Wis. Other reactants, such as epibromohydrin and 1-bromo-3,4-epoxybutane, are likewise commercially available or may be readily prepared by those skilled in the art using commonly employed synthetic methodology.

REACTION SCHEME 1

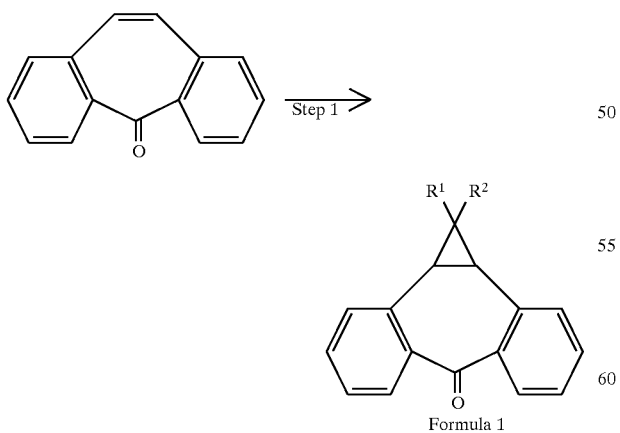

-continued
REACTION SCHEME 1

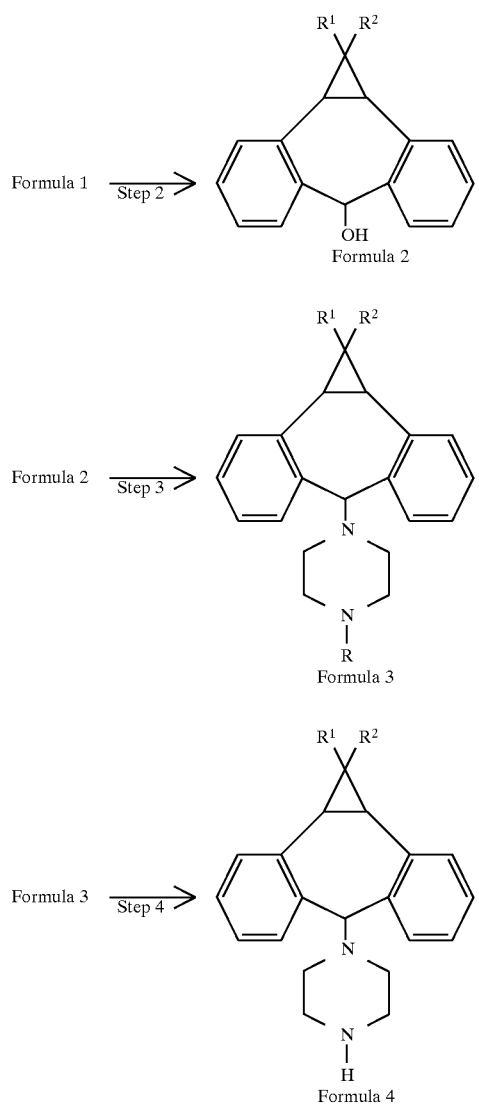

Formula 4
+
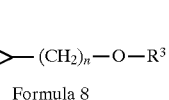
Formula 8 or

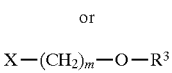
Formula 9

$\xrightarrow{\text{Step 5}}$

-continued
REACTION SCHEME 1

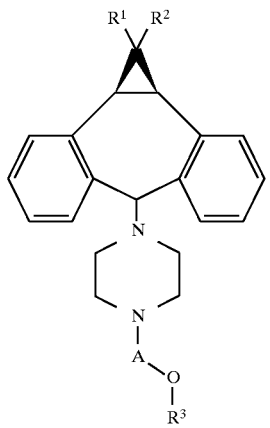

Formula 1

Preparation of Formula 1

A solution of an acetate (such as sodium chlorodifluoroacetate, methyl trichloroacetate, ethyl trifluoroacetate; depending upon the desired substituents for $R^1$ and $R^1$) in a solvent (such as diglyme, benzene, or petroleum ether) is added over a period of 4 to 8 hours (preferably 6 hours) to a solution of dibenzosuberenone (for example in diglyme) with stirring and under nitrogen, maintaining the reaction temperature at 160°–165° C. (Other reaction temperatures may be employed depending upon the reactants used, as described in Ciganek, et al. and in Coyne and Cusic.) The reaction mixture is brought to room temperature, then poured into water and extracted (e.g., with ether). The desired 10,11-substituted-methanodibenzosuberone is isolated and purified by conventional means, for example, the organic (e.g., benzene) phase is washed with water, dried (e.g., over $Na_2SO_4$), evaporated, and the residue is recrystallized (e.g., from ethanol, and optionally again, e.g, from acetone/hexane).

Alternatively, compounds of Formula 2 where $R^1$ and $R^2$ are not identical, such as H and Cl, respectively, can be prepared as described in *J.Med.Chem.*, Vol. 17, 72 (1974), incorporated herein by reference. The compound of Formula 2 where $R^1$ and $R^2$ are both hydrogen can be prepared as described in Coyne and Cusic, "Aminoalkyldibenzo[a,e]cyclopropa[c]cycloheptene Derivatives. A Series of Potent Antidepressants," *J.Med.Chem.*, 1974, Vol. 17, No. 1, 72–75, previously incorporated herein by reference.

Preparation of Formula 2

A solution of an 10,11-(optionally substituted)-methanodibenzosuberone in a solvent (e.g., THF/methanol) is cooled (e.g., in an ice bath) and a reducing agent (e.g., sodium borohydride) is added in portions. The reaction mixture is allowed to come to room temperature and stirred for 1 to 5 hours (preferably 2 hours), then poured into water. The product is isolated (e.g., by filtration) and purified by conventional means (e.g., washed with water and dried) to give the corresponding 10,11-(optionally substituted)-methanodibenzosuberol.

Preparation of Formula 3

A solution of an 10,11-(optionally substituted)-methanodibenzosuberol in a solvent (e.g., dioxane) is cooled (e.g., in an ice bath) followed by halogenation [e.g,. by dropwise addition of thionyl chloride, maintaining an elevated temperature (40 to 70° C., preferably 50° C.) for 2 to 5 hours (preferably 4 hours)]. The reaction mixture is evaporated to dryness, giving a mixture of syn- and anti-isomers of the corresponding 5-halo-10,11-(optionally substituted)-methanodibenzosuberane. This halogenated suberane is, without further purification, dissolved (e.g., in acetonitrile) and a piperazine is introduced by nucleophilic displacement of the halide [e.g., by adding 1-piperazinecarboxaldehyde with stirring, preferably under dry $N_2$ at elevated temperature (e.g., 100° C.) for 10 to 30 hours (preferably 20 hours)]. The reaction mixture is evaporated to dryness and the desired 1-[10,11-(optionally substituted)-methanodibenzosuber-5-yl]-4-formylpiperazine product is isolated and purified by conventional means [e.g., the residue is partitioned between aqueous $NaHCO_3$ and ethyl acetate, the organic phase washed with water, dried (e.g., over $K_2CO_3$) and evaporated]. The individual syn- and anti- isomers are separated, e.g., by flash chromatography of the residue on silica gel (30% acetone/hexane).

Preparation of Formula 4

A solution of a 1-[10,11-(optionally substituted) methanodibenzosuber-5-yl]-4-formyl-piperazine and potassium hydroxide in a solvent (e.g., 9:1. ethanol/$H_2O$) is refluxed for 0.5 to 2 hours (preferably 1 hour), then cooled. The cooled reaction mixture is concentrated, diluted with water, extracted (e.g., with ethyl acetate), dried (e.g., over $K_2CO_3$), and the organic phase is evaporated to give the corresponding 1-[10,11- (optionally substituted) methanodibenzosuber-5-yl]piperazine.

Preparation of Formula I

A solution of a compound of Formula 8 [e.g., a 1-(aryloxy or heteroaryloxy)-2,3-epoxypropane or a 1-(aryloxy or heteroaryloxy)-3,4-epoxybutane] or an aryloxy- or heteroaryloxyalkyl halide of Formula 9 and a 1-[10,11-(optionally substituted)methanodibenzosuber-5-yl] piperazine is refluxed in a solvent (e.g., isopropanol) for 10 to 30 hours (preferably 20 hours). The desired product, a corresponding 10,11-methanodibenzosuberane derivative of Formula I, is isolated and purified by conventional means (for example, evaporated to dryness and chromatographed on silica gel (e.g., using 70:30:1 ethyl acetate/hexane/triethylamine)].

REACTION SCHEME 2

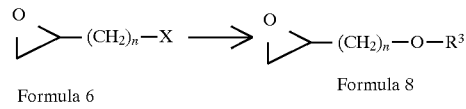

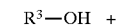

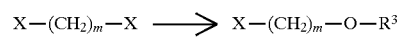

 

Preparation of Formula 8

An aryl- or heteroaryl alcohol (such as benzofurazan-4-ol, quinolin-5-ol, or 2-nitrophenol), dissolved in a solvent (e.g., acetonitrile, THF, or dimethyl formamide) is treated with a slight excess of a strong base (e.g., sodium hydride or potassium t-butoxide). The mixture is heated (e.g., at 50° C.) for 10 minutes to 2 hours (preferably 30 minutes). A compound of Formula 6 (such as 1-chloro-2,3-expoxybutane, 1-bromo-2,3-epoxybutane, epibromohydrin, epichlorohydrin, or a tosyl or nosyl derivative thereof) is added and the mixture is heated (e.g., at 60° C. for 1 to 5 hours; preferably 2 hours). The reaction mixture is poured into water and extracted (e.g., with ethyl acetate). The organic phase is washed with water, dried over $Na_2SO_4$, and evaporated to give the corresponding 1-(aryloxy or heteroaryloxy)-2,3-epoxypropane or 1-(aryloxy or heteroaryloxy)-3,4-epoxybutane, which is isolated and purified by conventional means [e.g., chromatographed on silica gel (50% ethyl acetate/hexane)].

The compounds of Formula 8, such as 1-(5-quinolinyloxy)-2,3-epoxypropane can also be synthesized as described in *Drug Design and Discovery*, Vol. 9, 69 (1992), incorporated herein by reference.

Preparation of Formula 9

As illustrated in Reaction Scheme 2, the anion of an aryl- or heteroaryl alcohol of Formula 5 is reacted with a dihaloalkyl compound of Formula 7, such as 1-bromo-2-chloroethane, 1-bromo-3-chloropropane or 1-bromo-4-chlorobutane, in a solvent (such as acetone, THF, or DMF) at a temperature ranging from room temperature to the boiling point of the solvent employed, to give the corresponding haloalkyloxyaryl compound of Formula 9. This synthesis is described in U.S. Pat. No. 5,112,817, previously incorporated herein by reference.

REACTION SCHEME 3

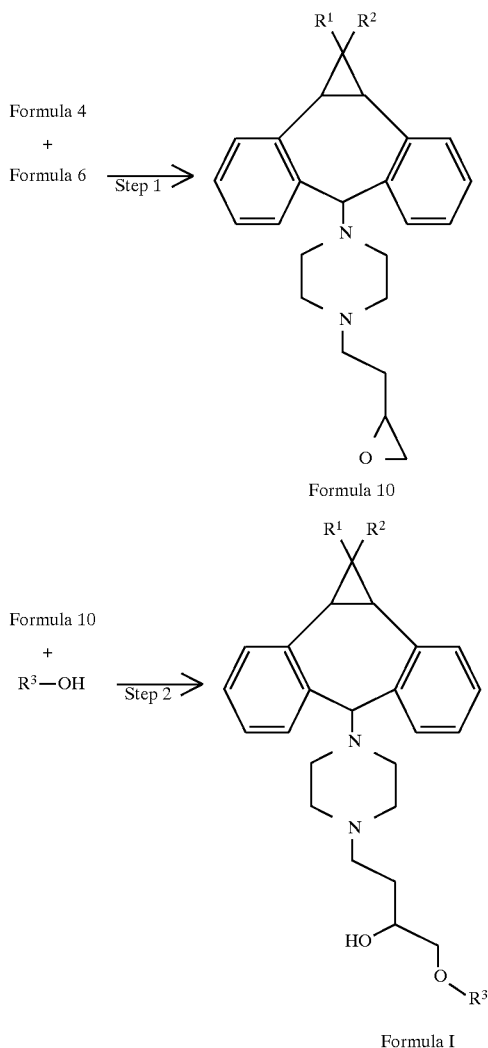

Formula I

Preparation of Formula 10

As illustrated in Reaction Scheme 3, Step 1, a 1-[10,11-(optionally substituted)-methanodibenzosuber-5-yl] piperazine of Formula 4 is reacted with a compound of Formula 6 (e.g., the compound where n is 2 is illustrated in Reaction Scheme 3; other compounds of Formula 6 will give corresponding products) under the conditions described above in connection with the Preparation of Formula 8 (in Reaction Scheme 2), to give a 1-[10,11-(optionally substituted)-methanodibenzosuber-5-yl]-4-(3,4-epoxybutyl) piperazine compound of Formula 10.

Preparation of Formula I Where $R^b$ is OH

As illustrated in Reaction Scheme 3, Step 2, a 1-[10,11-(optionally substituted)-methanodibenzosuber-5-yl]-4-(3,4-epoxybutyl)piperazine compound of Formula 10 is reacted with an aryl- or heteroaryl alcohol (such as benzofurazan-4-ol, quinolin-5-ol, or 2-nitrophenol), under the conditions described above in connection with the Preparation of Formula I (in Reaction Scheme 1), to give the corresponding compound of Formula 1 where $R^b$ is OH.

Formula I Where $R^a$ or $R^b$ is Lower Acyloxy

The compounds of Formula I where $R^a$ or $R^b$ is lower acyloxy are prepared as described in U.S. Pat. No. 5,112,817, previously incorporated by reference, starting from the corresponding compound of Formula I where $R^a$ or $R^b$ is OH (prepared as described above). For example, a compound of Formula I where $R^a$ or $R^b$ is OH is reacted with an acyl chloride to generate the corresponding acyloxy compound.

Preparation of the Salts of Formula I

The compounds of Formula I can be converted to corresponding acid addition salts. The conversion is accomplished by treatment with a stochiometric amount of an appropriate acid, such as hydrochloric acid (e.g., 3 molar equivalents to form the trihydrochloride salt). Typically, the free base is dissolved in a polar organic solvent, such as methanol or ethanol, and the acid is added in water, methanol or ethanol. The temperature is maintained at 0° C. to 50° C. The corresponding salt precipitates spontaneously or can be brought out of solution with a less polar solvent.

The acid addition salts of the compounds of Formula I can be decomposed to the corresponding free bases by treatment with an excess of a suitable base, such as ammonia or sodium bicarbonate, typically in the presence of an aqueous solvent, and at a temperature between 0° C. and 50° C. The free base is isolated by conventional means, such as extraction with an organic solvent.

Preferred Processes and Last Steps

A 1-(aryloxy or heteroaryloxy)-2,3-epoxypropane or a 1-(aryloxy or heteroaryloxy)-3,4-epoxybutane, or an aryloxy- or heteroaryloxyalkyl halide, and a 1-[10,11-(optionally substituted)methanodibenzosuber-5-yl] piperazine are combined to give the corresponding 10,11-methanodibenzosuberane derivative of Formula I.

A compound of Formula I where $R^a$ or $R^b$ is OH is reacted with an acyl chloride to generate the corresponding acyloxy compound.

A compound of Formula I is contacted with a pharmaceutically acceptable acid to form the corresponding acid addition salt.

A pharmaceutically acceptable acid addition salt of Formula I is contacted with a base to form the corresponding free base of Formula I.

Preferred Compounds

Preferred are the compounds of Formula 1 where $R^1$ and $R^2$ are fluoro. Also preferred are those compounds where A is 2-hydroxypropylene. Also preferred are those compounds where $R^3$ is 5-quinolyl. Further preferred are those compounds which combine the above-mentioned features. Certain single isomers are also preferred.

Most preferred is the compound 5-{3-[4-(10,11-difluoromethanodibenzosuber-5-yl)piperazin-1-yl)-2-hydroxypropoxy)-quinoline; particularly the (2R)-anti isomer thereof.

Utility, Testing and Administration
General Utility

The compounds of the present invention are chemosensitizing or potentiating agents, and are also useful as resistance modifying agents. They are useful for treating multidrug resistance (i.e., after clinical resistance becomes evident), and can also be administered at the time of initial chemotherapy (i.e., before any clinical resistance becomes evident) to enhance the activity of anticancer agents when first administered. The compounds of the present invention are also useful for the treatment of drug-resistant malaria.

Testing

In vitro activity for chemosensitizing or potentiating agents, particularly for treating multidrug resistance, is determined by an MTT Proliferation Assay, for example a modification of the assay described in Mosmann, T. "Rapid Colorimetric Assay For Cellular Growth And Survival: Application to proliferation and cytotoxicity assays," *J. Immunol. Meth.*, Vol. 65, 55–63 (1983). Another MTT Proliferation Assay is described in Alley, et al., "Feasibility of Drug Screening with Panels of Human Tumor Cell Lines Using a Microculture Tetrazolium Assay," *Cancer Research*, Vol. 48, 589–601 (1988).

In vivo activity for chemosensitizing or potentiating agents, particularly for treating multidrug resistance, is determined, for example, as described in Slate and Michelson, "Drug Resistance Reversal Strategies: A Comparison Of Experimental Data With Model Predictions," *J. Natl. Cancer Inst.*, Vol. 83, 1574–1580 (1991). Other in vivo testing procedures are described in Sato, et al., "Circumvention of Multidrug Resistance by a Newly Synthesized Quinoline Derivative, MS-073," *Cancer Research*, Vol. 51, 2420–2424 (1991); Tsuruo, et al., "Circumvention of Vincristine and Adriamycin Resistance in Vitro and in Vivo by Calcium Influx Blockers," *Cancer Research*, Vol. 43, 2905–2910 (1983); and Tsuruo, et al., "Overcoming of Vincristine Resistance in P388 Leukemia in Vivo and in Vitro through Enhanced Cytotoxicity of Vincristine and Vinblastine by Verapamil," *Cancer Research*, Vol. 41, 1967–1972 (1981).

Aqueous stability of the compounds is determined by conventional procedures, e.g., by measuring the amount of a compound remaining in solution at various pH values and temperatures.

Administration

The compounds of Formula 1 are administered at a therapeutically effective dosage, e.g., a dosage sufficient to provide treatment for the disease states previously described, typically by co-administration with a second active agent, preferably a cancer chemotherapeutic agent, and most preferably, a cancer chemotherapeutic agent to which clinical resistance has become evident in the mammal being treated. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.01 to 4.0 mg/kg of body weight, preferably about 0.1 to 2.0 mg/kg of body weight, and most preferably about 0.3 to 1.0 mg/kg of body weight. Thus, for administration to a 70 kg person, the dosage range would be about 0.7 to 280 mg per day, preferably about 7.0 to 140 mg per day, and most preferably about 21 to 70 mg per day. The amount of active compound administered will, of course, be dependent on the subject and disease state being treated, the severity of the affliction, the manner and schedule of administration (e.g., oral administration one day prior to cancer chemotherapy and intravenous administration during cancer chemotherapy) and the judgment of the prescribing physician.

In employing the compounds of this invention for treatment of the above conditions, any pharmaceutically acceptable mode of administration can be used. The compounds of Formula I can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or a pharmaceutically acceptable salt thereof. In addition, these compositions may include other medicinal agents, pharmaceutical agents, carriers, adjuvants, etc., such as cancer chemotherapeutic agents.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like.

Preferably the compositions will take the form of a pill or tablet. Thus the composition will contain along with the active ingredient: a diluent such as lactose, sucrose, dicalcium phosphate, or the like; a lubricant such as magnesium stearate or the like; and a binder such as starch, gum acacia, gelatin, polyvinylpyrrolidine, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975.

The composition or formulation to be administered will, in any event, contain a quantity of the active compound in an amount sufficient to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%–95% active ingredient, preferably 0.1–50%.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Suitability for oral and parenteral administration is another advantage of the present invention, due to the superior stability characteristics that have been found for compounds of Formula I, a problem identified with MS-073.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01 to 10% in solution are employable, and will be higher if the composition is a solid which will be subsequently diluted to the above percentages. Preferably the composition will comprise 0.2–2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

Example 1

10,11-Difluoromethanodibenzosuberone
1A. Formula 1 where $R^1$ and $R^2$ are F

A solution of sodium chlorodifluoroacetate (350 g) in diglyme (1400 ml) was added dropwise during 6 hours to a solution of dibenzosuberenone (25 g) in diglyme (500 ml), with overhead stirring and under nitrogen, maintaining the reaction temperature at 160°–165° C. The cooled reaction mixture was poured into water (1.8 l) and extracted with ether (1.8 l). The organic phase was washed with water, dried over $Na_2SO_4$, and evaporated. The residue was recrystallized from ethanol, then from acetone/hexane to give 14 g of 10,11-difluoromethanodibenzosuberone, mp 149.6° C. Flash chromatography of the combined mother liquors on silica gel, eluting with 20% acetone/hexane, gave-an additional 6.5 g of the desired material.

1B. Formula 1 varying $R^1$ and $R^2$

By following the procedure of part A, and substituting sodium chlorodifluoroacetate with the following:
a. methyl trichloroacetate,
b. methyl tribromoacetate, and
c. sodium dichlorofluoroacetate;
there are obtained the following respective compounds:
a. 10,11-dichloromethanodibenzosuberone,
b. 10,11-dibromomethanodibenzosuberone, and
c. 10,11-chlorofluoromethanodibenzosuberone;

Example 2

10,11-Difluromethanodibenzosuberol
2A. Formula 3 where $R^1$ and $R^2$ are F

A solution of 10,11-difluoromethanodibenzosuberone (20.4 g) in THF/MeOH (1:2, 900 ml) was cooled in an ice bath. Sodium borohydride (12 g) was added in portions. The cooling bath was removed, the reaction mixture was stirred at ambient temperature for 2 hours, and poured into water. The product was filtered off, washed with water, and dried to give 20 g of 10,11-difluromethanodibenzosuberol, mp 230.1°–230.6° C.

2B. Formula 2 varying $R^1$ and $R^2$

By following the procedure of part A, and substituting 10,11-difluromethanodibenzosuberone with the following:
a. 10,11-dichloromethanodibenzosuberone,
b. 10,11-dibromomethanodibenzosuberone,
c. 10,11-methanodibenzosuberone, and
d. 10,11-chlorofluoromethanodibenzosuberone;
there are obtained the following respective compounds:
a. 10,11-dichloromethanodibenzosuberol,
b. 10,11-dibromomethanodibenzosuberol,
c. 10,11-methanodibenzosuberol, and
d. 10,11-chlorofluoromethanodibenzosuberol.

Example 3

Syn- and Anti- 1-(10,11-Difluoromethanodibenzosuber-5-yl)-4-formylpiperazine

3A. Formula 3 where $R^1$ and $R^2$ are F, and R is Formyl

To a solution of 10,11-difluromethanodibenzosuberol (5.2 g) in dioxane (70 ml), cooled in an ice bath, was added thionyl chloride (4.5 ml) dropwise. The temperature was raised to 50° C. and maintained for four hours. The reaction mixture was evaporated to dryness, giving a mixture of syn- and anti-5-chloro-10,11-difluoromethanodibenzosuberane (5.7 g), which was dissolved in acetonitrile (200 ml) and 1-piperazinecarboxaldehyde (10 ml) was added. The mixture was stirred under dry $N_2$ at 100° C. (bath temperature) for 20 hours and then evaporated to dryness. The residue was partitioned between aqueous $NaHCO_3$ and ethyl acetate. The organic phase was washed with water, dried over $K_2CO_3$, and evaporated. Flash chromatography of the residue on silica gel (30% acetone/hexane) gave syn-1-(10,11-difluoromethanodibenzosuber-5-yl)-4-formyl-piperazine (2.4 g), mp 213° C., and anti-1-(10,11-difluoromethanodibenzosuber-5-yl)-4-formylpiperazine (2.6 g), mp 238° C.

3B. Formula 3 varying $R^1$ and $R^2$

By following the procedure of part A, and substituting 10,11-difluromethanodibenzosuberol with the following:
a. 10,11-dichloromethanodibenzosuberol,
b. 10,11-dibromomethanodibenzosuberol,
c. 10,11-methanodibenzosuberol, and
d. 10,11-chlorofluoromethanodibenzosuberol;
there are obtained the following respective compounds:
a1. anti-1-(10,11-dichloromethanodibenzosuber-5-yl)-4-formylpiperazine, mp 205° C.,
a2. syn-1-(10,11-dichloromethanodibenzosuber-5-yl)-4-formylpiperazine,
b1. anti-1-(10,11-dibromomethanodibenzosuber-5-yl)-4-formylpiperazine,
b2. syn-1-(10,11-dibromomethanodibenzosuber-5-yl)-4-formylpiperazine,
c1. anti-1-(10,11-methanodibenzosuber-5-yl)-4-formylpiperazine, mp 195° C.,
c2. syn-1-(10,11-methanodibenzosuber-5-yl)-4-formylpiperazine,
d1. anti-1-(10,11-chlorofluoromethanodibenzosuber-5-yl)-4-formylpiperazine, and
d2. syn-1-(10,11-chlorofluoromethanodibenzosuber-5-yl)-4-formylpiperazine.

Example 4

Anti-1-(10,11-difluoromethanodibenzosuber-5-yl) piperazine

4A. Formula 4 where $R^1$ and $R^2$ are F

A solution of anti-1-(10,11-difluoromethanodibenzosuber-5-yl)-4-formylpiperazine (2.55 g) and potassium hydroxide (3.0 g) in ethanol/$H_2O$ (9:1, 100 ml) was refluxed for 1 hour, then cooled. The cooled reaction mixture was concentrated, diluted with water, extracted with ethyl acetate and dried over $K_2CO_3$. The dried organic phase was evaporated to give anti-1-(10, 11-difluoromethanodibenzosuber-5-yl)piperazine (2.35 g), mp 131° C.

4B. Formula 4 varying $R^1$ and $R^2$

By following the procedure of part A, and substituting anti-1-(10,11-difluoromethanodibenzosuber-5-yl)-4-formylpiperazine with the following:
a. syn-1-(10,11-difluoromethanodibenzosuber-5-yl)-4-formylpiperazine,
b. anti-1-(10,11-dichloromethanodibenzosuber-5-yl)-4-formylpiperazine,
c. syn-1-(10,11-dichloromethanodibenzosuber-5-yl)-4-formylpiperazine,
d. anti-1-(10,11-dibromomethanodibenzosuber-5-yl)-4-formylpiperazine,
e. syn-1-(10,11-dibromomethanodibenzosuber-5-yl)-4-formylpiperazine,
f. anti-1-(10,11-methanodibenzosuber-5-yl)-4-formylpiperazine,
g. syn-1-(10,11-methanodibenzosuber-5-yl)-4-formylpiperazine,
h. anti-1-(10,11-chlorofluoromethanodibenzosuber-5-yl)-4-formylpiperazine, and
i. syn-1-(10,11-chlorofluoromethanodibenzosuber-5-yl)-4-formylpiperazine;
there are obtained the following respective compounds:
a. syn-1-(10,11-difluoromethanodibenzosuber-5-yl) piperazine, mp 225.5° C.,
b. anti-1-(10,11-dichloromethanodibenzosuber-5-yl) piperazine, mp 199° C.,
c. syn-1-(10,11-dichloromethanodibenzosuber-5-yl) piperazine,
d. anti-1-(10,11-dibromomethanodibenzosuber-5-yl) piperazine,
e. syn-1-(10,11-dibromomethanodibenzosuber-5-yl) piperazine,
f. anti-1-(10,11-methanodibenzosuber-5-yl)piperazine, mp 103° C.,
g. syn-1-(10, 11-methanodibenzosuber-5-yl)piperazine,
h. anti-1-(10,11-chlorofluoromethanodibenzosuber-5-yl) piperazine, and
i. syn-1-(10,11-chlorofluoromethanodibenzosuber-5.-yl) piperazine.

Example 5

1-(4-Benzofurazanyloxy)-2,3-epoxypropane

5A. Formula 8 where $R^3$ is Benzofuran and n is 1

Sodium hydride (620 mg; 60% oil dispersion) was added in portions to benzofurazan-4-ol (1.74 g) in dimethyl formamide (30ml). The mixture was heated at 50° C. for 30 min. Epibromohydrin (1.6 ml) was added and the mixture was heated at 60° C. for 2 hours. The reaction mixture was poured into water and extracted with ethyl acetate. The organic phase was washed with water, dried over $Na_2SO_4$, and evaporated. The residue was chromatographed on silica gel (50% ethyl acetate/hexane) to give 1-(4-benzofurazanyloxy)-2,3-epoxypropane (1.6 g), mp 75° C.

5B. Formula 8 varying $R^3$ and n

By following the procedure of part A, and substituting benzofurazan-4-ol and epibromohydrin with the following:
a. quinolin-5-ol and 1-chloro-3,4-epoxybutane,
b. 2-nitrophenol and epibromohydrin,
c. 2-chlorophenol and epibromohydrin,
d. 2-difluoromethoxyphenol and epibromohydrin,
e. pyridin-3-ol and epibromohydrin, and
f. quinolin-5-ol and epibromohydrin;
there are obtained the following respective compounds:
a. 1-(5-quinolinyloxy)-3,4-epoxybutane,
b. 1-(2-nitrophenoxy)-2,3-epoxypropane,
c. 1-(2-chlorophenoxy)-2,3-epoxypropane,
d. 1-(2-difluoromethoxyphenoxy)-2,3-epoxypropane,
e. 1-(3-pyridyloxy)-2,3-epoxypropane, and
f. 1-(5-quinolinyloxy)-2,3-epoxypropane.

5C. Formula 9 varying $R^3$ and n

By following the procedure of part A and substituting benzofurazan-4-ol and epibromohydrin with the following:

a. quinolin-5-ol and 1-bromo-3-chloropropane,
b. quinolin-5-ol and 1-bromo-4-chlorobutane,
c. 2-nitrophenol and 1-bromo-3-chloropropane;
there are obtained the following respective compounds:
a. 1-(5-quinolinyloxy)-3-chloropropane,
b. 1-(5-quinolinyloxy)-4-chlorobutane, and
c. 1-(2-nitrophenoxy)-3-chloropropane.

Example 6

(2R,S)-Anti-5-(3-[$^4$-(10,11-difluoromethanodibenzosuber-5-yl)piperazin-1-yl]-2-hydroxypropoxy}quinoline 6A. Formula I where $R^1$ and $R^2$ are F, A is (2R,S)-Hydroxypropyl, and $R^3$ in 5-Quinolyl A solution of 1-(5-quinolinyloxy)-2,3-epoxypropane (586 mg) and anti-1-(10,11-difluoromethanodibenzosuber-5-yl)piperazine (950 mg) in isopropanol (20 ml) was refluxed for 20 hours. The reaction mixture was evaporated to dryness and the residue was chromatographed on silica gel (70:30:1 ethyl acetate/hexane/triethylamine) to give (2R,S)-anti-5-{3-[4-(10,11-difluoromethanodibenzosuber-5-yl)piperazine-1-yl]-2-hydroxypropoxy}-quinoline (1.33 g), which was converted to the trihydrochloride salt, mp 193.5° C., by reaction with 3 molar equivalents of HCl.

6B. Formula I Isomers varying $R^1$, $R^2$, $R^3$ and A

By following the procedure of part A, and substituting anti-1-(10,11-difluoromethanodibenzosuber-5-yl)piperazine and 1-(5-quinolinyloxy)-2,3-epoxypropane with the following:

a. syn-1-(10,11-difluoromethanodibenzosuber-5-yl)piperazine and 1-(5-quinolinyloxy)-2,3-epoxypropane,
b. anti-1-(10,11-difluoromethanodibenzosuber-5-yl)piperazine and (2R)-1-(5-quinolinyloxy)-2,3-epoxypropane,
c. anti-1-(10,11-difluoromethanodibenzosuber-5-yl)piperazine and (2S)-1-(5-quinolinyloxy)-2,3-epoxypropane,
d. syn-1-(10,11-difluoromethanodibenzosuber-5-yl)piperazine and (2R)-1-(5-quinolinyloxy)-2,3-epoxypropane,
e. syn-1-(10,11-difluoromethanodibenzosuber-5-yl)piperazine and (2S)-1-(5-quinolinyloxy)-2,3-epoxypropane,
f. anti-1-(10,11-dichloromethanodibenzosuber-5-yl)piperazine and 1-(5-quinolinyloxy)-2,3-epoxypropane,
g. anti-1-(10,11-dichloromethanodibenzosuber-5-yl)piperazine and (2R)-1-(5-quinolinyloxy)-2,3-epoxypropane,
h. anti-1-(10,11-dichloromethanodibenzosuber-5-yl)piperazine and (2S)-1-(5-quinolinyloxy)-2,3-epoxypropane,
i. anti-1-(10,11-methanodibenzosuber-5-yl)piperazine and 1-(5-quinolinyloxy)-2,3-epoxypropane,
j. anti-1-(10,11-difluoromethanodibenzosuber-5-yl)piperazine and 1-(4-benzofurazanyloxy)-2,3-epoxypropane,
k. syn-1-(10,11-difluoromethanodibenzosuber-5-yl)piperazine and 1-(4-benzofurazanyloxy)-2,3-epoxypropane,
l. anti-1-(10,11-dichloromethanodibenzosuber-5-yl)piperazine and 1-(4-benzofurazanyloxy)-2,3-epoxypropane,
m. anti-1-(10,11-difluoromethanodibenzosuber-5-yl)piperazine and 1-(2-nitrophenoxy)-2,3-epoxypropane,
n. anti-1-(10,11-difluoromethanodibenzosuber-5-yl)piperazine and 1-(2-chlorophenoxy)-2,3-epoxypropane,
o. anti-1-(10,11-difluoromethanodibenzosuber-5-yl)piperazine and 1-(2-difluoromethoxyphenoxy)-2,3-epoxypropane,
p. anti-1-(10,11-difluoromethanodibenzosuber-5-yl)piperazine and 1-(3-pyridyloxy)-2,3-epoxypropane,
q. anti-1-(10,11-difluoromethanodibenzosuber-5-yl)piperazine and 1-(5-quinolinyloxy)-3-chloropropane,
r. anti-1-(10,11-difluoromethanodibenzosuber-5-yl)piperazine and 1-(5-quinolinyloxy)-4-chlorobutane,
s. anti-1-(10,11-difluoromethanodibenzosuber-5-yl)piperazine and 1-(2-nitrophenoxy)-3-chloropropane, and
t. anti-1-(10,11-difluoromethanodibenzosuber-5-yl)piperazine and 1-(5-quinolinyloxy)-3,4-epoxybutane, there are obtained the following respective compounds:
a. (2R,S)-syn-5-{3-[4-(10,11-difluoromethanodibenzosuber-5-yl)piperazin-1-yl-2-hydroxypropoxy}quinoline, mp 208° C. (trihydrochloride),
b. (2R)-anti-5-{3-[4-(10,11-difluoromethanodibenzosuber-5-yl)piperazin-1-yl]-2-hydroxypropoxy}quinoline, mp 190° C. (trihydrochloride),
c. (2S)-anti-5-{3-(4-(10,11-difluoromethanodibenzosuber-5-yl)piperazin-1-yl]]2-hydroxypropoxy}quinoline, mp 195° C. (trihydrochloride),
d. (2R)-syn-5-{3-[4-(10,11-difluoromethanodibenzosuber-5-yl)piperazin-1-yl]-2-hydroxypropoxy}quinoline, mp 193° C. (trihydrochloride),
e. (2S)-syn-5-{3-[4-(10,11-difluoromethanodibenzosuber-5-yl)piperazin-1-yl]-2-hydroxypropoxy}quinoline, mp 188.5° C. (trihydrochloride),
f. (2R,S)-anti-5-{3-[4-(10,11-dichloromethanodibenzosuber-5-yl)piperazin-1-yl]-2-hydroxypropoxy}quinoline, mp 195° C. (trihydrochloride),
g. (2R)-anti-5-{3-[4-(10,11-dichloromethanodibenzosuber-5-yl)piperazin-1-yl]-2-hydroxypropoxy}quinoline, mp 218° C. (trihydrochloride),
h. (2S)-anti-5-{3-[4-(10,11-dichloromethanodibenzosuber-5-yl)piperazin-1-yl]-2-hydroxypropoxy}quinoline, mp 215° C. (trihydrochloride),
i. (2R,S)-anti-5-{3-[4-(10,11-methanodibenzosuber-5-yl)piperazin-1-yl]-2-hydroxypropoxy}quinoline,
j. (2R,S)-anti-4-{3-[4-(10,11-difluoromethanodibenzosuber-5-yl)piperazin-1-yl]-2-hydroxypropoxy}benzofurazan, mp 186° C. (dihydrochloride),
k. (2R,S)-syn-4-{3-[4-(10,11-difluoromethanodibenzosuber-5-yl)piperazin-1-yl]-2-hydroxypropoxy}benzofurazan, mp 188° C. (dihydrochloride),
l. (2R,S)-anti-4-{3-[4-(10,11-dichloromethanodibenzosuber-5-yl)piperazin-1-yl]-2-hydroxypropoxy}benzofurazan,
m. (2R,S)-anti-1-{3-[4-(10,11-difluoromethanodibenzosuber-5-yl)piperazin-1-yl]-2-hydroxypropoxy}-2-nitrobenzene,
n. (2R,S)-anti-1-{3-[4-(10,11-difluoromethanodibenzosuber-5-yl)piperazin-1-yl]-2-hydroxypropoxy}-2-chlorobenzene,
o. (2R,S)-anti-1-{3-[4-(10,11-difluoromethanodibenzosuber-5-yl)piperazin-1-yl]-2-hydroxypropoxy}-2-difluoromethoxybenzene,
p. (2R,S)-anti-3-{3-[4-(10,11-difluoromethanodibenzosuber-5-yl)piperazin-1-yl]-2-hydroxypropoxy}pyridine,
q. (2R,S)-anti-5-{3-[4-(10,11-difluoromethanodibenzosuber-5-yl)piperazin-1-yl]-propoxy}quinoline,
r. (2R,S)-anti-5-{4-[4-(10,11-difluoromethanodibenzosuber-5-yl)piperazin-1-yl]-butoxy}quinoline, s. (2R,S)-anti-5-{3-[4-(10,11-difluoromethanodibenzosuber-5-yl)piperazin-1-yl]-propoxy}-2-nitrobenzene, and t. (2R,S)-anti-5-{3-[4-(10,11-difluoromethanodibenzosuber-5-yl)piperazin-1-yl]-3-hydroxybutoxy}quinoline.

Example 7

This example illustrates the preparation of a representative pharmaceutical formulation for oral administration containing an active compound of Formula I, e.g., (2R)-anti-5-{3-[4-(10,11-difluoromethanodibenzosuber-5-yl)piperazin-1-yl]-2-hydroxypropoxy}quinoline.

| Ingredients | Quantity per tablet, mgs. |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1–6, can be used as the active compound in the preparation of the orally administrable formulations of this example.

Example 8

This example illustrates the preparation of another representative pharmaceutical formulation for oral administration, containing an active compound of Formula I, e.g., (2R)-anti-5-{3-[4-(10,11-difluoromethanodibenzosuber-5-yl)-piperazin-1-yl]-2-hydroxypropoxy}quinoline.

| Ingredients | Quantity per tablet, mgs. |
| --- | --- |
| Active compound | 400 |
| cornstarch | 50 |
| lactose | 145 |
| magnesium stearate | 5 |

The above ingredients are mixed intimately and pressed into single scored tablets.

Other compounds of Formula I, such as those prepared in accordance with Examples 1–6, can be used as the active compound in the preparation of the orally administrable formulations of this example.

Example 9

This example illustrates the preparation of a representative pharmaceutical formulation containing an active compound of Formula I, e.g., (2R)-anti-5-{3-[4-(10,11-difluoromethanodibenzosuber-5-yl)piperazin-1-yl]-2-hydroxypropoxy}quinoline.

A suspension for oral administration is prepared having the following composition:

| Ingredients | Amount |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Other compounds of Formula I, such as those prepared in accordance with Examples 1–6, can be used as the active compound in the preparation of the orally administrable formulations of this example.

Example 10

This example illustrates the preparation of a representative pharmaceutical formulation containing an active compound of Formula I, e.g., (2R)-anti-5-{3-[4-(10,11-difluoromethanodibenzosuber-5-yl)piperazin-1-yl]-2-hydroxypropoxy}quinoline.

An injectable preparation buffered to a pH of 4 is prepared having the following composition:

| Ingredients | Amount |
| --- | --- |
| Active compound | 0.2 g |
| Sodium Acetate Buffer Solution (0.4M) | 2.0 ml |
| HCl (1N) | q.s. to pH 4 |
| water (distilled, sterile) | q.s. to 20 ml |

Other compounds of Formula I, such as those prepared in accordance with Examples 1–6, can be used as the active compound in the preparation of the injectable formulations of this example.

Example 11

This example illustrates the preparation of a representative pharmaceutical formulation containing an active compound of Formula I, e.g., (2R)-anti-5-{3-[4-(10,11-difluoromethanodibenzosuber-5-yl)piperazin-1-yl]-2-hydroxypropoxy}quinoline.

A suppository totalling 2.5 grams is prepared having the following composition:

| Active compound | 500 mg |
| --- | --- |
| witepsol H-15* | balance |

(*triglycerides of saturated vegetable fatty acid; a product of Riches-Nelson, Inc., New York, N. Y.).

Other compounds of Formula I, such as those prepared in accordance with Examples 1–6, can be used as the active compound in the preparation of the suppository formulations of this example.

Example 12

Determination of Stability at Acid pH

Test compounds (15 μg) were dissolved in 3 ml of 0.01 N HCl (pH 2) and incubated at 37° C. At various times, 10 μl aliquots were withdrawn and injected into a 3 μm Pecosphere C-18 cartridge column (3.3×0.46 cm) for HPLC analysis (mobile phase: 35% acetonitrile/18% tetrahydrofuran/47% potassium phosphate monobasic, containing 4 mM N,N-dimethyloctylamine; flow rate 1.0 ml/min). The test compounds and their degradation products were monitored by UV absorption at 240 nm. Disappearance of the parent compound was expressed as a percent peak height relative to time zero, from which $t_{1/2}$ values were determined graphically, as follows.

MS-073, $t_{1/2}$=15 minutes, (2R,S)-anti-5-{3-[4-(10,11-methanodibenzosuber-5-yl) piperazine-1-yl]-2-hydroxypropoxy}quinoline, $t_{1/2}$= 2.5 hours, (2R,S)-5-{3-[4-(10,11-difluoromethanodibenzosuber-5-yl)piperazine-1-yl]-2-hydroxypropoxy}quinoline, $t_{1/2}$= >72 hours, and (2R,S)-anti-5-{3-[4-(10,11-chloromethanodibenzosuber-5-yl)piperazine-1-yl]-2-hydroxypropoxy}quinoline, $t_{1/2}$>72 hours.

The compounds of the present invention exhibit stability at acid pH, improved over MS-073, when tested by this method.

Example 13

Determination of Activity in Vitro Utilizing the MTT Assay

This is a modification of the assay described by Mosmann, T. in "Rapid Colorimetric Assay For Cellular Growth And Survival: Application to proliferation and cytotoxicity assays," *J. Immunol. Meth.*, Vol. 65, 55–63 (1983).

Cell stock (0.3 ml) containing multidrug resistant $CH^RC5$ Chinese hamster cells (about $2\times10^5$ cells/ml) is combined with medium (2.7 ml) containing the compound to be tested or a vehicle control, in the presence or absence of adriamycin (1 μg/ml) to form a suspension. Aliquots (0.1 ml) of the cell suspension are then plated into eight wells-in each of three 96-well microtiter plates. After incubation in a tissue culture incubator at 37° C., one plate is removed at each of the following time points: 24 hours, 48 hours and 72 hours. Upon removal from the incubator, 3-[4,5-dimethylthiazol-2-yl]-2,5-diphenyl tetrazolium bromide, MTT (10 μl, from a stock solution of 5 mg/ml in phosphate buffered saline) is added to each well of the plate, which is then returned to the incubator for three hours.

The formazan crystals generated by the activity of mitochondrial enzymes in living cells are solubilized by aspirating off the medium and adding DMSO (150 μl/well) with mixing performed on an orbital shaker. A570 (reference wavelength 650 nm) is read on a Molecular Devices microplate reader, and results are expressed as a percentage of vehicle control or adriamycin control each day or as a graph of A570 over time.

The compounds of the present invention show activity when tested by this method.

Example 14

Determination of Activity in Vivo Utilizing the MDR Assay

This is a modification of the assay described by Slate and Michelson, in "Drug Resistance Reversal Strategies: A Comparison Of Experimental Data With Model Predictions," *J. Natl. Cancer Inst.*, Vol. 83, 1574–1580 (1991).

Mice (B6D2F1, female, 7–8 weeks, approx. 20 gm, Jackson Laboratory) are randomized, weighed, and divided into groups of 6–7 each. On day 0 each mouse is injected ip with 0.2 ml of P388/ADR multidrug resistant murine leukemia cells, $2.4\times10^7$ cells/ml. Two hours later, each mouse is implanted ip with an Alzet 7-day minipump (Model 2001, Alza Corporation, Palo Alto, Calif.) containing the vehicle (DMSO/PBS) plus adriamycin (3 mg/kg/day), a test compound alone (30 mg/kg/day) or adriamycin (3 mg/kg/day) plus a test compound (at 0.3, 3, 10 and 30 mg/kg/day). The mice are monitored daily and deaths recorded starting on day 7. Survival time increased over the vehicle control and adriamycin groups indicates activity.

The compounds of the present invention show activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A chemosensitizing method for enhancing bioavailability of a pharmaceutically active agent comprising administering to a mammal in need thereof an amount of a compound represented by the formula

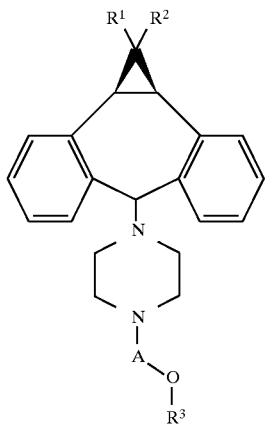

or a pharmaceutically acceptable salt thereof, wherein:

A is —$CH_2$—$CH_2$—, —$CH_2$—$CHR^a$—$CH_2$— where $R^a$ is H, OH or lower acyloxy, or —$CH_2$—$CHR^a$—$CHR^b$—$CHR^b$—$CH_2$— where one of $R^a$ or $R^b$ is H, OH or lower acyloxy and the other is H;

$R^1$ is H, F, Cl or Br;

$R^2$ is H, F, Cl or Br, with the proviso that when taken together $R^1$ and $R^2$ are not both F, Cl or Br; and R³ is heteroaryl or optionally substituted phenol where the substituents are selected from F, Cl, Br, CF₃, CN, NO₂ and OCHF₂;

sufficient to increase permeation of said active agent through the blood-brain barrier.

2. A chemosensitizing method for enhancing bioavailability of a pharmaceutically active agent comprising administering to a mammal in need thereof an amount of a compound represented by the formula

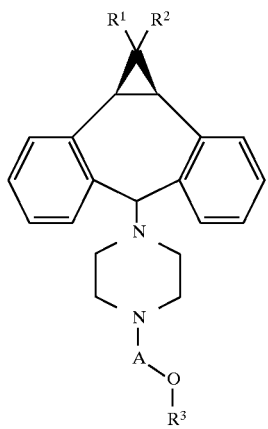

or a pharmaceutically acceptable salt thereof, wherein:

A is —CH₂—CH₂, —CH₂—CHR$^a$—CH₂— where R$^a$ is H, OH or lower acyloxy, or —CH₂—CHR$^a$—CHR$^b$—CH₂— where one of R$^a$ or R$^b$ is H, OH or lower acyloxy, and the other is H;

R¹ is H, F, Cl or Br;

R² is H, F, Cl or Br, with the proviso that when taken together R¹ and R² are not both F, Cl or Br; and R³ is heteroaryl or optionally substituted phenyl where the substituents are selected from F, Cl, Br, CF₃, CN, NO₂ and OCHF₂;

sufficient to increase permeation of said active agent through the gastrointestinal tract.

3. A chemosensitizing method for enhancing bioavailability of a pharmaceutically active agent comprising administering to a mammal in need thereof an amount of a compound represented by the formula

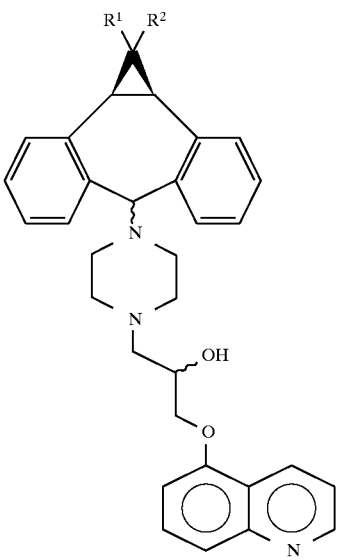

or a pharmaceutically acceptable salt thereof, wherein R¹ and R² are independently selected from H, F, Cl or BR, with the priviso that R¹ and R² when taken together are not both F, Cl or Br, sufficient to increase permeation of said active agent through the blood-brain barrier.

4. The method of claim 3 wherein R¹ and R² are H.

5. The method of claim 4 wherein the compound is represented by the formula

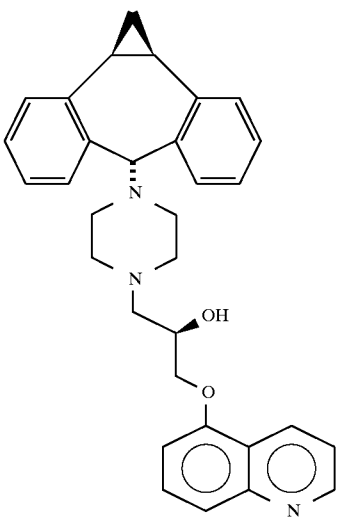

6. A chemosensitizing method for enhancing bioavailability of a pharmaceutically active agent comprising administering to a mammal in need thereof an amount of a compound represented by the formula

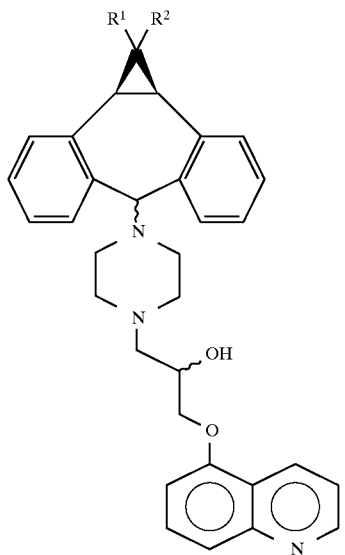

or a pharmaceutically acceptable salt thereof, wherein $R^1$ and $R^2$ are independently selected from H, F, Cl or Br, with the proviso that $R^1$ and $R^2$ when taken together are not both F, Cl or Br, sufficient to increase permeation of said active agent through the gastrointestinal tract.

7. The method of claim 6 wherein $R^1$ and $R^2$ are H.

8. The method of claim 7 wherein the compound is represented by the formula

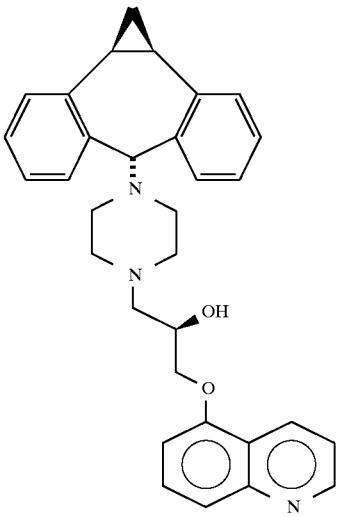

* * * * *

UNITED STATES PATENT AND TRADEMARK OFFICE
CERTIFICATE OF CORRECTION

PATENT NO. : 5,874,434
DATED : Feb. 23, 1999
INVENTOR(S) : Pfister et al.

It is certified that error appears in the above-identified patent and that said Letters Patent is hereby corrected as shown below:

Claim 1, at column 24, line 62 "$CHR^b$—$CHR^b$—$CH_2$— where one of $R^a$ or $R^b$ is H," should read -- $CHR^b$—$CH_2$— where one of $R^a$ or $R^b$ is H --.

Signed and Sealed this

Thirteenth Day of July, 1999

Q. TODD DICKINSON

Attest:

Attesting Officer

Acting Commissioner of Patents and Trademarks